(12) United States Patent
Zhong et al.

(10) Patent No.: US 12,109,425 B2
(45) Date of Patent: Oct. 8, 2024

(54) METHOD FOR CARTILAGE REGENERATION, MAGNETIC PULSE DEVICE AND COIL APPLIED FOR MAGNETIC PULSE DEVICE

(71) Applicant: Hefei Institutes of Physical Science, Chinese Academy of Sciences, Anhui (CN)

(72) Inventors: Kai Zhong, Anhui (CN); Xiaoming Zhang, Anhui (CN); Jin Zhang, Anhui (CN); Haiyang Tong, Anhui (CN); Hongyi Yang, Anhui (CN)

(73) Assignee: Hefei Institutes of Physical Science, Chinese Academy of Sciences, Hefei (CN)

( * ) Notice: Subject to any disclaimer, the term of this patent is extended or adjusted under 35 U.S.C. 154(b) by 0 days.

(21) Appl. No.: 15/733,409

(22) PCT Filed: Jan. 24, 2018

(86) PCT No.: PCT/CN2018/073983
§ 371 (c)(1),
(2) Date: Jul. 22, 2020

(87) PCT Pub. No.: WO2019/144316
PCT Pub. Date: Aug. 1, 2019

(65) Prior Publication Data
US 2021/0093880 A1    Apr. 1, 2021

(51) Int. Cl.
*A61N 2/02*    (2006.01)
*A61N 2/00*    (2006.01)

(52) U.S. Cl.
CPC ............... *A61N 2/004* (2013.01); *A61N 2/02* (2013.01)

(58) Field of Classification Search
CPC . A61N 2/00; A61N 2/02; A61N 2/004; A61N 2/006; A61N 2/008
(Continued)

(56) References Cited

U.S. PATENT DOCUMENTS 5,067,940 A * 11/1991 Liboff ...................... A61N 2/02
                                                            600/13
5,131,904 A *  7/1992 Markoll ................... A61N 2/02
                                                            600/14
(Continued)

FOREIGN PATENT DOCUMENTS

CN        87213121 U      3/1988
CN        203494061 U     3/2014
(Continued)

OTHER PUBLICATIONS

"International Application Serial No. PCT/CN2018/073983, International Search Report mailed Oct. 22, 2018", w/ English Translation, (Oct. 22, 2018), 7 pgs.
(Continued)

*Primary Examiner* — Samuel G Gilbert
(74) *Attorney, Agent, or Firm* — Schwegman Lundberg & Woessner, P.A.

(57) ABSTRACT

A method and a device for cartilage regeneration are provided. The method for cartilage regeneration has steps of: applying a pulse magnetic field with a magnetic pulse device to a body part of a mammal in which an injured cartilage tissue is located, wherein the magnetic pulse device has a magnetic pulse generator and a coil, and by applying a magnetic pulse with a frequency of from 10 Hz to 200 Hz to the coil, a uniform magnetic field distribution is produced in a region of the body part covered by the coil, thereby achieving a uniform magnetically induced electrical excitation. The method can effectively facilitate articular cartilage (Continued)

regeneration, and is convenient to operate, having a broad prospect in clinical applications.

12 Claims, 6 Drawing Sheets

(58) Field of Classification Search
USPC .................................................. 600/9–15
See application file for complete search history.

(56) References Cited

U.S. PATENT DOCUMENTS

| | | | |
|---|---|---|---|
| 5,195,941 A | 3/1993 | Erickson et al. | |
| 5,415,617 A | 5/1995 | Kraus | |
| 2002/0151760 A1* | 10/2002 | Paturu | A61N 2/02 600/15 |
| 2003/0158585 A1* | 8/2003 | Burnett | A61N 1/36021 607/2 |
| 2011/0098523 A1* | 4/2011 | Kraus | A61N 2/02 600/13 |
| 2012/0172653 A1* | 7/2012 | Chornenky | A61N 1/40 600/14 |
| 2013/0072746 A1 | 3/2013 | Burnett et al. | |
| 2015/0196772 A1 | 7/2015 | Ghiron et al. | |

FOREIGN PATENT DOCUMENTS

| | | |
|---|---|---|
| CN | 105326638 A | 2/2016 |
| JP | 2006296669 A | 11/2006 |
| WO | 9944685 | 9/1999 |
| WO | 0115770 | 3/2001 |
| WO | WO-0231845 A1 | 4/2002 |
| WO | WO-2006115120 A1 | 11/2006 |
| WO | 2013049345 | 4/2013 |

OTHER PUBLICATIONS

"International Application Serial No. PCT/CN2018/073983, Written Opinion mailed Oct. 22, 2018", (Oct. 22, 2018), 5 pgs.
"European Application Serial No. 18902851.7, European Search Report dated Aug. 19, 2021", (Aug. 19, 2021), 8 pgs.
"European Application Serial No. 18902851.7, Communication pursuant to Article 94(3) EPC mailed Jan. 10, 2024", 4 pgs.

* cited by examiner

METHOD FOR CARTILAGE REGENERATION, MAGNETIC PULSE DEVICE AND COIL APPLIED FOR MAGNETIC PULSE DEVICE

PRIORITY APPLICATIONS

This application is a U.S. National Stage Filing under 35 U.S.C. § 371 from International Application No. PCT/CN2018/073983, filed on Jan. 24, 2018, and published as WO2019/144316 on Aug. 1, 2019; the benefit of priority of which is hereby claimed herein, and which application and publication are hereby incorporated herein by reference in its entirety.

TECHNICAL FIELD

The present disclosure relates to the technical field of medical care, and particularly to a method and a device for cartilage regeneration.

BACKGROUND

Repair of cartilage injury is an unsolved problem in the medical field. Currently, magneto-electric therapy (MET) only acts as an auxiliary physical therapy, and mainly relies on a low-intensity magnetic pulse treatment using a continuous wave with a frequency of from tens to hundreds kHz. However, current MET methods do not exhibit the ability to facilitate cartilage regeneration.

SUMMARY

The inventors have carried out intensive researches and discovered that magneto-electric therapy is not only related to the magnetically induced electrical field, but also directly related to the magnetically induced current in a tissue. The induced current in the tissue can not only act on individual cells, but also act on the whole macroscopic tissue, changing the medium and signal transmission between tissues, thereby influencing and facilitating the recovery of cartilage tissue on multiple levels. The large scale bioelectrical effect can also increase the blood circulation around a joint, facilitating the improvement of histotrophic nutrition. Muscle tissues around the joint can also be reflexively activated by the electrical stimulation so as to mitigate muscle spasm, increase the ability of the joint to withstand pressure, increase the flexion and extension angle of the joint, and restore the joint function. On this basis, the inventors surprisingly discover that articular cartilage regeneration can be achieved with the stimulation of a magnetic pulse (in particular a high intensity magnetic pulse) at a specific frequency, and thus the present invention is completed.

The present disclosure aims to provide a method for cartilage regeneration, a magnetic pulse device and a coil for the magnetic pulse device.

In one aspect, the present disclosure provides a method for cartilage regeneration, comprising: applying a pulse magnetic field with a magnetic pulse device, to a body part of a mammal in which an injured cartilage tissue is located, wherein the magnetic pulse device comprises a magnetic pulse generator and a coil, and by applying a magnetic pulse with a frequency of from 10 Hz to 200 Hz, preferably from 20 Hz to 80 Hz, and more preferably from 40 Hz to 60 Hz, to the coil, a uniform magnetic field distribution is produced in a region of the body part covered by the coil, thereby achieving a uniform magnetically induced excitation.

In some embodiments, a duration of the magnetic pulse is from 1 microsecond (μsec) to 1 millisecond (msec), and preferably from 200 μsec to 500 μsec.

In some embodiments, an intensity of the magnetic pulse is from 10 Gauss (G) to 30,000 G, for example, from 100 G to 10,000 G, or from 1000 G to 8000 G.

In some embodiments, a total duration for each treatment (i.e., the time for applying the magnetic field to the body part) is from 1 minute to 30 minutes, and a total treatment numbers is from 10 to 500, and preferably from 30 to 300.

In some embodiments, a repetition frequency of the treatment may be once per day or every 2 days, or twice per day.

In some embodiments, a pulse number for each treatment is from 1000 to 10000, and preferably from 4000 to 8000.

In some embodiments, the cartilage tissue comprises an articular cartilage tissue. For example, the articular cartilage tissue comprises finger, wrist, elbow, knee, ankle, shoulder, and hip articular cartilage tissues.

In some embodiments, the mammal comprises human, rabbit, dog, cattle, horse, sheep and pig.

In another aspect, the present disclosure further provides a magnetic pulse device, comprising: a magnetic pulse generator and a coil, wherein the coil has a shape conformal with a topological structure of an animal's joint, and is made by winding one or more wires in a pattern which is formed from an axial projection of uniformly distributed concentric structures (such as concentric circles and concentric squares) on a surface of the topological structure, such that when a magnetic pulse is applied to the coil, a uniform magnetic field distribution is produced in a region effectively covered by the coil.

In some embodiments, the topological structure comprises a saddle type, a hemisphere type, a semi-cylinder type, a semi-birdcage type, and a half-spiral type structures, and the topological structure is corresponding to the geometry of a joint (such as finger, wrist, elbow, knee, ankle, shoulder, and hip joints).

In some embodiments, the magnetic field distribution produced by the coil is adjusted depending on the wire number and the wire density on the curved surface of the coil, so as to achieve a uniform magnetic field distribution in a region effectively covered by the coil.

In some embodiments, the magnetic pulse device further comprises a magnetic pulse controller which controls a frequency, a duration and an intensity of the magnetic pulse produced by the magnetic pulse generator and transmitted to the coil.

In some embodiments, the magnetic pulse controller controls the frequency of the magnetic pulse in a range from 10 Hz to 200 Hz, preferably from 20 Hz to 80 Hz, and more preferably from 40 Hz to 60 Hz.

In some embodiments, the magnetic pulse controller controls the intensity of the magnetic pulse in a range from 10 G to 30,000 G, for example, from 100 G to 10,000 G, or from 1000 G to 8000 G.

In some embodiments, the magnetic pulse controller controls the duration of the magnetic pulse in a range from 1 μsec to 1 msec, and preferably from 200 μsec to 500 μsec.

In some embodiments, the magnetic pulse device is used for cartilage regeneration.

In yet another aspect, the present disclosure further provides use of the magnetic pulse device as described above in preparing a device for cartilage regeneration.

In some embodiments, the device for cartilage regeneration is used for applying a magnetic field to a body part of a mammal in which an injured cartilage tissue is located, wherein by applying a magnetic pulse with a frequency of from 10 Hz to 200 Hz to the coil, a uniform magnetic field distribution is produced in a region of the body part covered by the coil, thereby achieving a uniform magnetically induced electrical excitation.

In still another aspect, the present disclosure further provides a coil for a magnetic pulse device, wherein the coil is made by winding one or more wires in a pattern which is formed from an axial projection of uniformly distributed concentric structures on a surface of a topological structure, such that when a magnetic pulse is applied to the coil, a uniform magnetic field distribution is produced in a region effectively covered by the coil.

In some embodiments, the topological structure comprises a saddle type, a parabola type, a hemi-ellipsoid type, a semi-cylinder type, a semi-birdcage type, and a half-spiral type structures, and the coil has a shape conformal with a geometry of a joint.

According to the present disclosure, articular cartilage regeneration can be effectively facilitated, and the method of the present disclosure is a non-invasive therapy and is convenient to operate, having a broad prospect in clinical applications.

DETAILED DESCRIPTION

The present disclosure will be further described in detail below with reference to the drawings.

Magnetic Pulse Device and Coil

Figure 1:
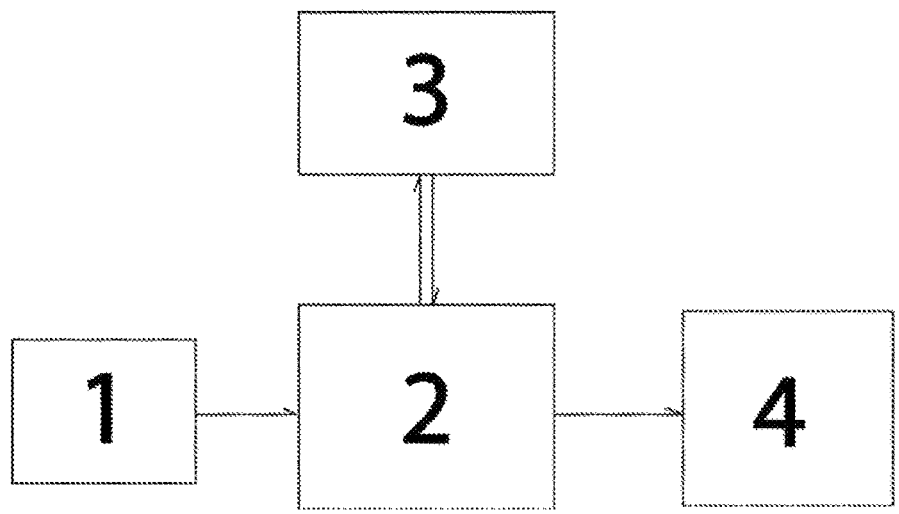
FIG. 1 is a schematic structural diagram of a magnetic pulse device according to an embodiment of the present disclosure.

FIG. 1 shows a schematic structural diagram of a magnetic pulse device according to an embodiment of the present disclosure, in which 1 represents a power source, 2 represents a magnetic pulse generator, 3 represents a magnetic pulse controller, and 4 represents a coil. Although FIG. 1 shows the power source 1, the power source 1 may of course be an external power source, and the magnetic pulse device itself may have no power source.

The magnetic pulse generator in the magnetic pulse device may be a magnetic pulse generator commonly used in the art, as long as it can generate the following pulses: magnetic pulses with an intensity controlled in a range of from 1 G to 10,000 G, a duration of from 0.1 μsec to 100 msec, and a frequency of from 0.1 Hz to 500 Hz.

The magnetic pulse controller is used for controlling the frequency, the duration and the intensity of the magnetic pulse generated by the magnetic pulse generator and transmitted to the coil. According to an embodiment, the magnetic pulse controller controls the magnetic pulse such that the frequency is in a range of from 10 Hz to 200 Hz, preferably from 20 Hz to 80 Hz, and more preferably from 40 Hz to 60 Hz; the intensity is in a range of from 10 G to 10,000 G, for example, from 100 G to 10,000 G, or from 1000 G to 8000 G; and the duration is in a range of from 1 μsec to 1 msec, preferably from 200 μsec to 500 μsec.

The coil in the magnetic pulse device is specifically designed depending on the entire structure of an application object (topological structure). The coil has a shape conformal with the topological structure, and is made by winding one or more wires in a pattern which is obtained from an axial projection of uniformly distributed concentric structures (such as concentric circles and concentric squares) on a surface of the topological structure, such that when a magnetic pulse is applied to the coil, a uniform magnetic field distribution is produced in a region effectively covered by the coil. The topological structure may be determined according to the geometry of a joint (such as finger, wrist, elbow, knee, ankle, shoulder and hip joints), for example, the topological structure may comprise a saddle type, a hemisphere type, a semi-cylinder type, a semi-birdcage type, and a half-spiral type structures. The magnetic field distribution produced by the coil may be adjusted depending on the wire number and the wire density on the curved surface of the coil, to achieve a desired uniform magnetic field distribution in a region effectively covered by the coil.

Figure 2:
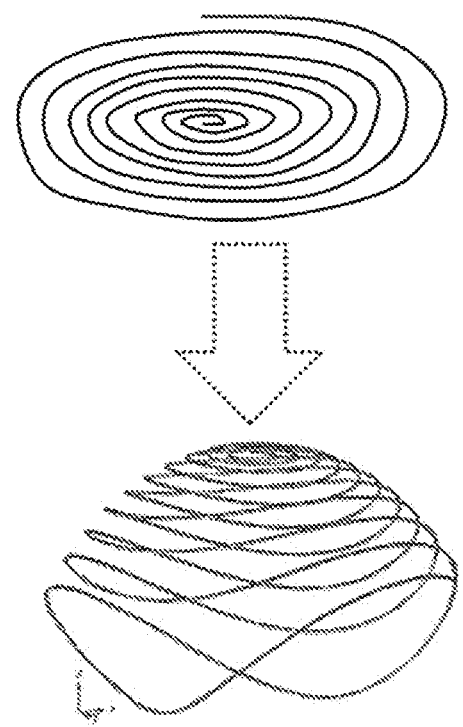
FIG. 2 is a schematic structural diagram of a coil according to the present disclosure.
Figure 3:
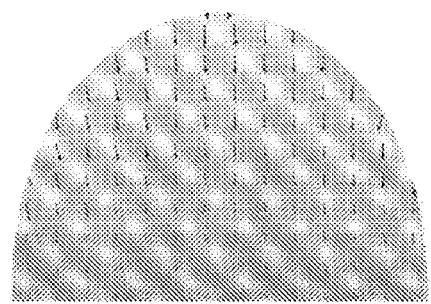
FIG. 3 is a schematic diagram of the magnetic field distribution produced by the coil shown in FIG. 2.

FIG. 2 shows a schematic structural diagram of a coil according to the present disclosure. The coil is similar to a hemisphere type, and is made by winding one wire in a pattern formed from an axial projection of uniformly distributed concentric circles on the surface of the hemisphere. FIG. 3 is a schematic diagram of the magnetic field distribution produced by the coil shown in FIG. 2. As seen from FIG. 3, the magnetic field is uniformly distributed in a region effectively covered by the coil.

Figure 4:
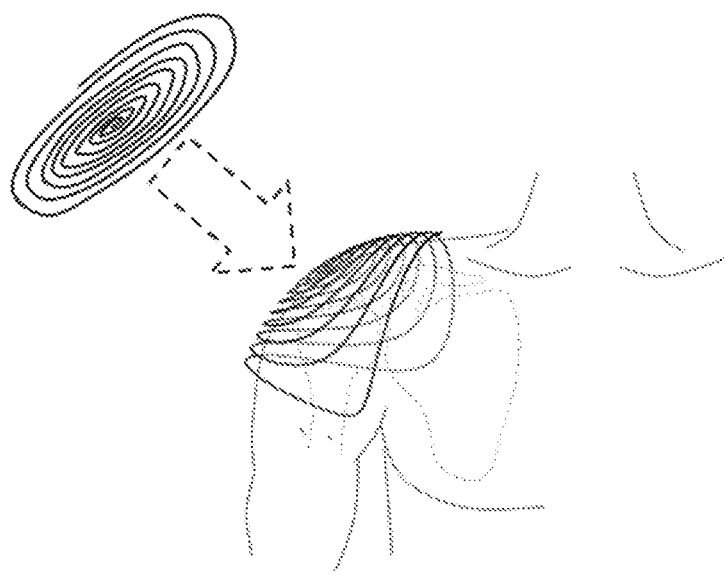
FIG. 4 is a schematic structural diagram of another coil according to the present disclosure.
Figure 5:
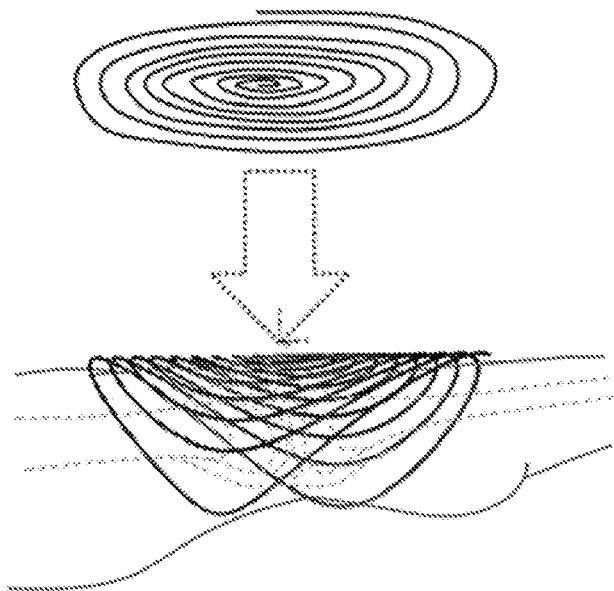
FIG. 5 is a schematic structural diagram of yet another coil according to the present disclosure.

FIG. 4 and FIG. 5 show two variants of the coil structure according the present disclosure, which respectively achieve a uniform magnetic field distribution similar to that as shown in FIG. 3 in respective effectively covered regions.

The magnetic pulse device of the present disclosure is preferably used for cartilage regeneration. Thus, the present disclosure further provides use of the magnetic pulse device as described above in preparing a device for cartilage regeneration.

According to some embodiments, the device for cartilage regeneration is used for applying a magnetic pulse to a body part of a mammal in which an injured cartilage tissue is located, so as to produce a uniform magnetic field distribution in a region of the body part covered by the magnetic pulse device, thereby achieving a uniform magnetic induction.

Method for Cartilage Regeneration

The present disclosure further provides a method for cartilage regeneration, comprising: applying with the magnetic pulse device as describe above a magnetic field to a body part of a mammal in which an injured cartilage tissue is located, wherein by applying a magnetic pulse with a frequency of from 10 Hz to 200 Hz to the coil of the magnetic pulse device, a uniform magnetic field distribution is produced in a region of the body part covered by the coil, thereby achieving a uniform magnetically induced excitation.

The frequency of the magnetic pulse for cartilage regeneration may be from 10 Hz to 200 Hz, preferably from 20 Hz to 80 Hz, and more preferably from 40 Hz to 60 Hz; the pulse duration may be from 1 μsec to 1 msec, and preferably 200 μsec to 500 μsec; and the pulse intensity may be from 10 G to 30,000 G, for example, from 100 G to 10,000 G, or from 1000 G to 8000 G.

According to some embodiments, a total duration for each treatment (i.e., the time for applying the magnetic field to the body part) is from 1 minute to 30 minutes, and a total treatment numbers is from 10 to 500, and preferably from 30 to 300. A repetition frequency of the treatment may be once per day or every 2 days, or twice per day. A pulse number for each treatment may be from 1000 to 10000, and preferably from 4000 to 8000.

According to some embodiments, the mammal may comprise human, rabbit, dog, cattle, horse, sheep, pig, and so on. The cartilage tissue may comprise an articular cartilage tissue. For example, the articular cartilage tissue comprises finger, wrist, elbow, knee, ankle, shoulder, and hip articular cartilage tissues.

EXAMPLES

Animal Modeling and Grouping

All animal experiments were approved by local animal ethics committee. Each of 36 New Zealand white rabbits (male, 4 to 6 months old, and weighed 2.8 to 3.0 kg) was fed in single cage. After one week, the animals were randomly grouped into 6 groups, i.e., a sham operation group, an injured cartilage model group, an 1 Hz magnetic pulse treatment group, a 20 Hz magnetic pulse treatment group, a 40 Hz magnetic pulse treatment group, and a sodium hyaluronate (SH) control group, and each group comprised of 6 animals having comparable body weights, with no statistically significant difference (P>0.05). The limbs and head of the experimental rabbit were fixed on an operating table, and the mouth and nose of the experimental rabbit were covered with an anesthetic mask. Anesthesia was induced and maintained by an isoflurane inhalation method, and the surgical operation was performed after the completion of the anesthesia. For the sham operation group, only the right knee joint capsule was incised. For other groups, the anterior cruciate ligament of the right knee joint was detached, and the medial meniscus was excised, so as to establish an osteoarthritis animal model. After joint instability was confirmed by a drawer test, the joint cavity was washed and sutured layer by layer. 600,000 U of penicillin was intramuscularly injected continuously for 3 days to prevent infection. After the surgical operation, the affected limb was not fixed to allow its free movement.

Treatment Method

The treatment started from $4^{th}$ Week after the surgical operation. The coil having a structure as shown in FIG. 2 was used. The pulse frequencies of the magnetic stimulator (Magstim, UK) were set to be 1 Hz, 20 Hz and 40 Hz respectively, the pulse intensity was set to be from 3000 to 5000, and the pulse duration was set to be from 300 to 500 μsec. In the treatment, the center of the coil was closely attached to the surface of the knee joint. The treatment was performed once per day, with 20 minutes for each treatment, 5 times per week, and 12 weeks in total. In the SH control group, the administration was carried out by injecting into the knee joint cavity, with 0.3 ml for each injection, once per week, and 12 weeks in total. No treatment was performed for the sham operation group and the model group.

MR Observation 9.4T magnetic resonance imaging inspection was performed on Week 4 and Week 13 after the surgical operation. The experimental rabbit was fixed on an operation table in a supine position, with the knee joint extended as straight as possible, and axial, coronal and sagittal scannings were performed on the knee joint. Three-dimension gradient recalled echo (3D-GRE) was used as the scanning sequence under the following conditions: TR/TE=20/9 ms, Matrix: 512×512×256, FOV: 50×50×50 mm$^3$, and layer thickness: 1 mm. MRI rating scale criterion of the articular cartilage was as follows. 0: cartilage surface profile is intact and thickness is normal; 1: layered structure of the cartilage disappears, and surface profile is mildly irregular; 2: cartilage surface is moderately irregular, and defect depth does not reach 50% of the entire layer thickness; 3: cartilage surface is very irregular, and defect depth exceeds 50% of the entire layer thickness, but cartilage is not completely detached; and 4: cartilage is lost in the whole layer and detached, and the subchondral bone is exposed. The image data were analyzed and evaluated individually by two or more high qualification image diagnosticians.

Determinations for Body Weight, Joint Motion Range, and IL-1β and NO in Serum

The body weight and the range of joint motion of the right knee joint (the maximal motion range of the joint when making flexion and extension movements) were measured on Week 13 after the surgical operation for the experimental rabbit in each group. Blood was taken from the ear vein. The serum was collected after centrifuging at 4000 r/min. The expression levels of IL-1β and NO were determined by ELISA method. The results were compared among the groups.

General and HE Staining Observations

The experimental rabbit was sacrificed by a venous embolism method on Week 13 after the surgical operation. The joint capsule was incised to expose the lower end of the femur. The injury conditions of condyle articular cartilages on the inner and outer sides of the femur were observed. The femur condyle of the right knee joint was cut into a sample of 0.4×0.3×0.2 cm$^3$. The sample was conventionally fixed, decalcified, embedded, sliced, and stained by an HE staining method. The change in histomorphology of the articular cartilage tissue was observed, and rated by Mankin's scale.

Statistical Method

Statistical treatment was performed by using SPSS18.0 software. The experimental data were expressed as mean value±standard deviation ($\bar{x}$±s). The groups were compared by an analysis of variance, and P<0.05 indicated that the difference was statistically significant.

Results
MRI Behaviors of the Knee Joint of the Experimental Rabbit on Week 4 and Week 13

On Week 4 after the surgical operation, for the sham operation group, the surface profile of the articular cartilage was intact, the thickness was normal, and the signal was uniform; for other groups, the cartilage layered structure disappeared, the surface profile of the cartilage was mildly irregular, some parts had defects, and the signal was not uniform, indicating that the model was successfully established (Table 1). On Week 13 after the surgical operation, the articular cartilage in the sham operation group was the same as that on Week 4; for most of the OA model group, the cartilage was lost in the whole layer and detached, and the subchondral bone was exposed; for the 1 Hz treatment group, the surface profile of the articular cartilage was irregular, the thickness and signal were not uniform, and the defect depth mostly exceeded 50% of the entire layer thickness, but the articular cartilage was not completely detached; for the 20 Hz treatment group, the surface profile of the articular cartilage was irregular, the thickness and signal were not uniform, but the cartilage defect depth mostly did not reach 50% of the entire layer thickness; for the 40 Hz treatment group, the surface profile of the articular cartilage was slightly irregular, but no obvious defect, the cartilage layer was slightly thickened, and the signal tended to be uniform; and for the sodium hyaluronate control group, the surface profile was slightly irregular, the signal was not uniform, and the partial cartilage defect depth mostly did not reach 50% of the entire layer thickness (Table 2).

TABLE 1

MRI scores of articular cartilage on Week 4

| MRI scores | Sham operation group (n = 6) | OA model group (n = 6) | 1 Hz treatment group (n = 6) | 20 Hz treatment group (n = 6) | 40 Hz treatment group (n = 6) | Sodium hyaluronate control group (n = 6) |
|---|---|---|---|---|---|---|
| 0 | 6 | 0 | 0 | 0 | 0 | 0 |
| 1 | 0 | 4 | 5 | 5 | 4 | 4 |
| 2 | 0 | 2 | 1 | 1 | 2 | 2 |
| 3 | 0 | 0 | 0 | 0 | 0 | 0 |
| 4 | 0 | 0 | 0 | 0 | 0 | 0 |

TABLE 2

MRI scores of articular cartilage on Week 13

| MRI scores | Sham operation group (n = 6) | OA model group (n = 6) | 1 Hz treatment group (n = 6) | 20 Hz treatment group (n = 6) | 40 Hz treatment group (n = 6) | Sodium hyaluronate control group (n = 6) |
|---|---|---|---|---|---|---|
| 0 | 6 | 0 | 0 | 0 | 0 | 0 |
| 1 | 0 | 0 | 0 | 1 | 4 | 2 |
| 2 | 0 | 1 | 1 | 4 | 1 | 3 |
| 3 | 0 | 4 | 5 | 1 | 1 | 1 |
| 4 | 0 | 1 | 0 | 0 | 0 | 0 |

Determinations for Body Weight, Joint Motion Range, and IL-1β and NO in Serum

Figure 7:
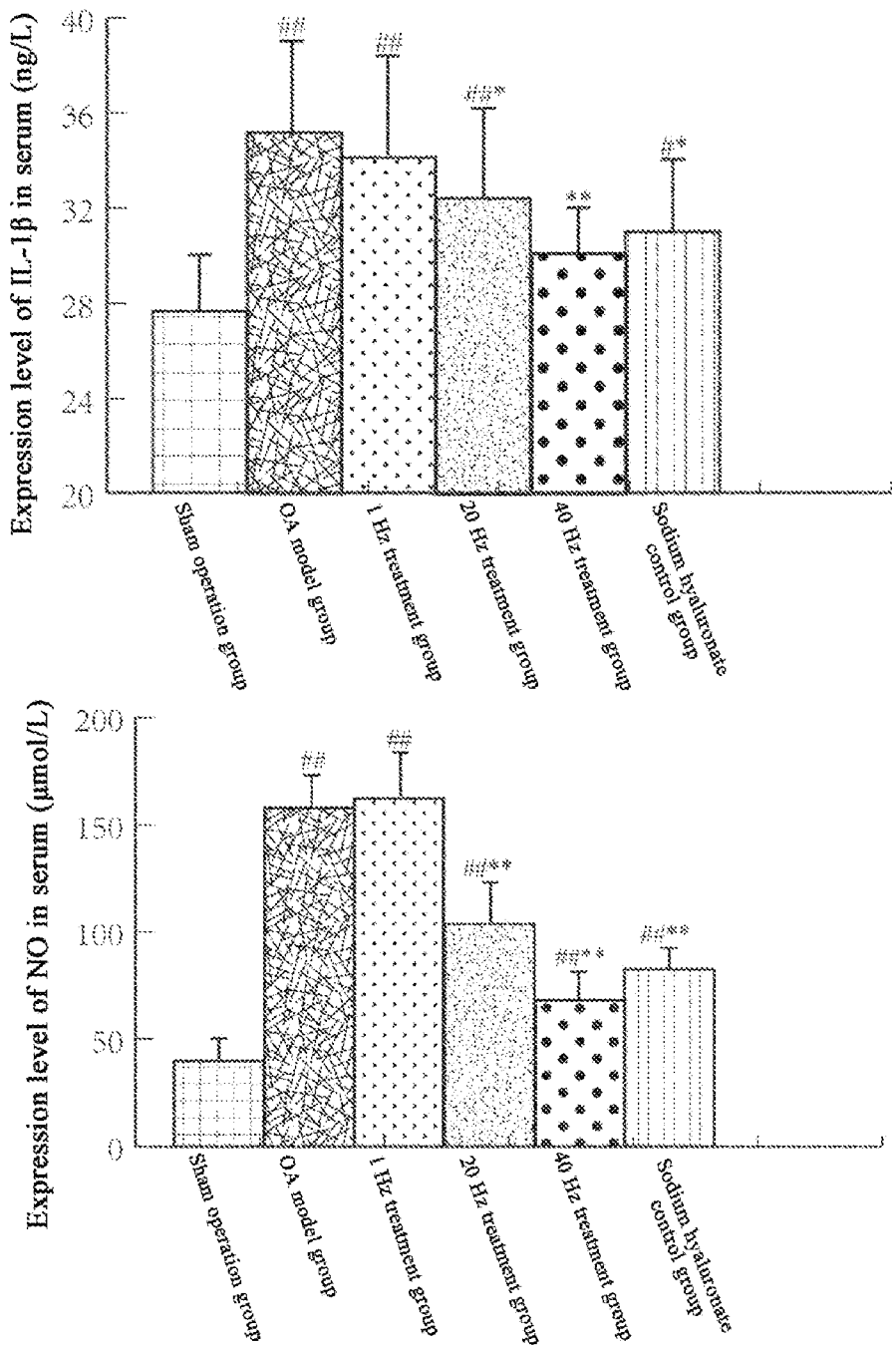
FIG. 7 shows the detection results of IL-1β and NO in serum for the groups in FIG. 6.

On Week 13, the body weights of the experimental rabbits were compared among the groups, and the difference was not statistically significant (P>0.05) (Table 3). As compared to the sham operation group, the joint motion ranges for the OA model group and the 1 Hz treatment group significantly decreased. With increasing the stimulation frequency, the knee joint motion ranges of the experimental rabbits in the 20 Hz treatment group and the 40 Hz treatment group tended to gradually increase. As compared to the OA model group, the difference was statistically significant (P<0.05 or P<0.01). The SH group also exhibited a significant improvement as compared to the OA model group (P<0.01) (Table 3). The IL-1β and NO levels in the serum were lower in the sham operation group, and were higher in the OA model group, with the difference being statistically significant (P<0.01). After magneto-electric therapy, those levels gradually decreased with the increase of the stimulation frequency, where, the IL-1β levels in the 20 Hz and 40 Hz treatment groups decreased significantly, with the difference being statistically significant (P<0.05 or P<0.01); the NO levels in the 1 Hz, 20 Hz and 40 Hz treatment groups all decreased, the NO level in the 40 Hz treatment group decreased the most significantly, and the difference was statistically significant (P<0.01). The IL-1β and NO levels in the sodium hyaluronate control group also exhibited a significant improvement as compared to the OA model group (P<0.05 or P<0.01) (FIG. 7).

TABLE 3

Body weights, joint motion ranges and Mankin's rating results of the experimental rabbits on Week 13

|  | Sham operation group (n = 6) | OA model group (n = 6) | 1 Hz treatment group (n = 6) | 20 Hz treatment group (n = 6) | 40 Hz treatment group (n = 6) | Sodium hyaluronate control group (n = 6) |
|---|---|---|---|---|---|---|
| Body weight (Kg) | 4.2 ± 0.3 | 4.1 ± 0.3 | 4.3 ± 0.3 | 4.2 ± 0.2 | 4.4 ± 0.2 | 4.4 ± 0.3 |
| Range of joint motion (°) | 143.3 ± 4.5 | 125.6 ± 4.6## | 125.9 ± 4.1## | 131.7 ± 2.6##* | 136.7 ± 4.0##** | 135.6 ± 5.3##** |
| Mankin's scores | 0.0 ± 0.0 | 10.3 ± 1.5## | 9.2 ± 1.3## | 8.0 ± 0.9##* | 5.8 ± 1.5##** | 6.0 ± 1.8##** |

As compared to the sham operation group, #P < 0.05, and ##P < 0.01.
As compared to the OA model group, *P < 0.05, and **P < 0.01.

General and HE Staining Observations

Figure 8:
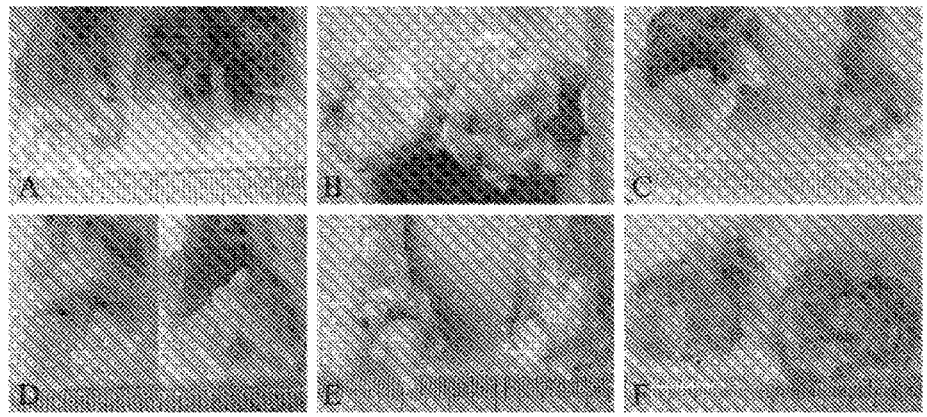
FIG. 8 shows a comparison of removed rabbit joints among the groups in Example 1.

As general observations, for the sham operation group, there was no swelling or stiffness at the right knee joint, and as seen when the joint capsule was opened, the surface of the joint was smooth and had a bright color; for the OA model group, the right knee joint swelled and was stiff, the surface of the articular cartilage was rough and anabrotic, spurs were formed on the periphery of the joint, and the gloss decreased; the 1 Hz treatment group had similar behaviors to those of the OA model group, having relatively severe injury; for the 20 Hz treatment group, the swelling of the right knee joint was significantly mitigated, there were defects and erosions on the surface of the articular cartilage, but the injury was relatively mild and had a limited range; for the 40 Hz treatment group, there was no obvious swelling or stiffness at the right knee joint, the surface of the cartilage was slightly rough, and the color was a little darker; and for the sodium hyaluronate control group, the swelling of the right knee joint was not obvious, and the surface of the cartilage was rough and slightly anabrotic (FIG. 8).

Figure 9:
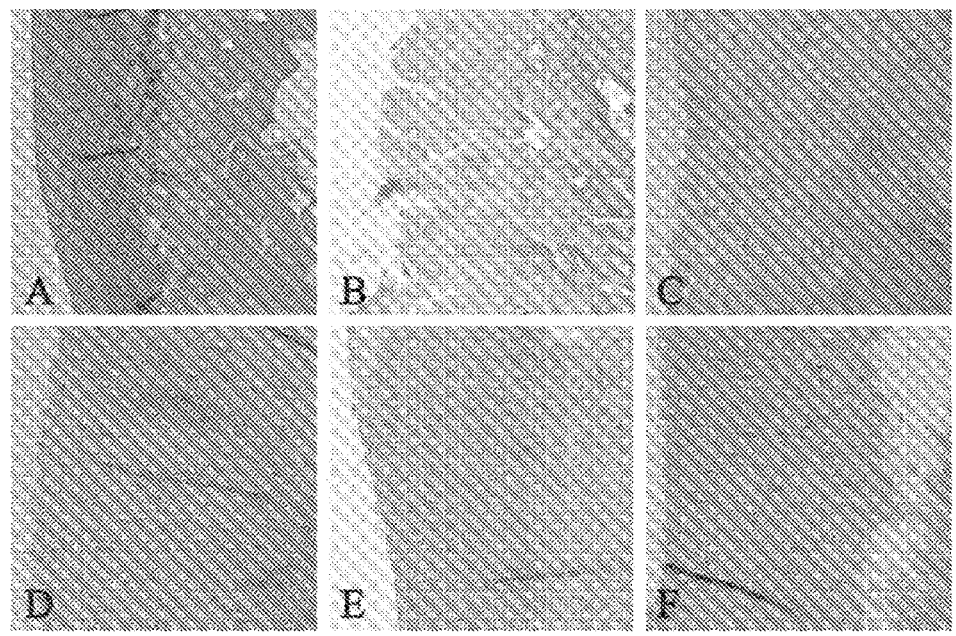
FIG. 9 shows the histological staining results of the joints for the groups in FIG. 8.
Figure 10:
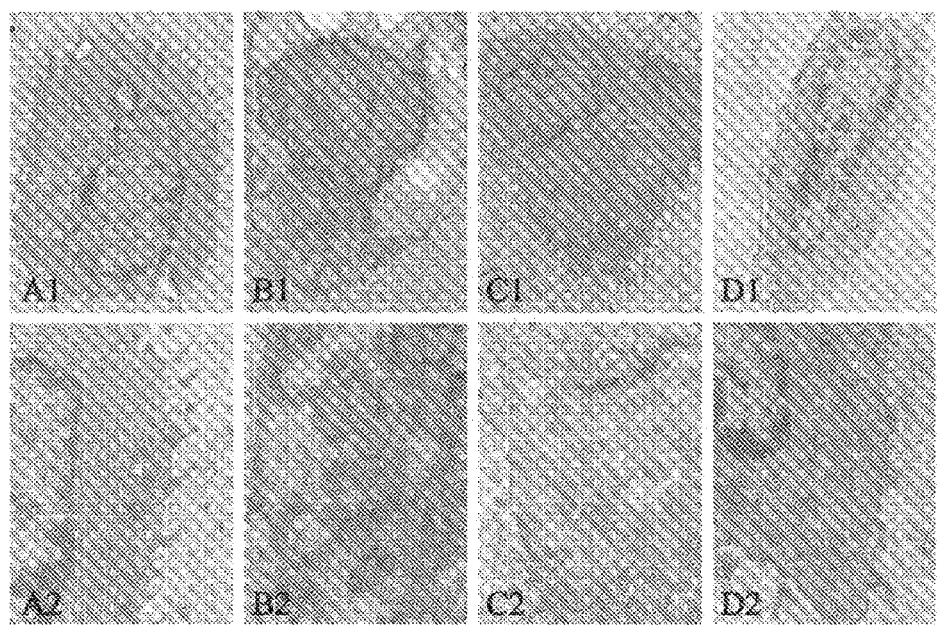
FIG. 10 shows the electron microscope results (with a magnification of 8,000 (for A1 to D1) and a magnification of 20,000 (for A2 to D2)) of the cartilage cells for the sham operation group, the injured cartilage model group, the 40 Hz magnetic pulse treatment group, and the sodium hyaluronate control group in FIG. 8.

As seen from the HE staining, for the sham operation group, the surface of the articular cartilage was smooth, the four-layered structure was clearly distinguishable, the layers were regularly arranged, the tidal lines were relatively clear and complete, and the bone cells had a spindle shape and were distributed uniformly; for the OA model group, the surface of the articular cartilage was rough, with relatively deep fissure, the integrity was destroyed, the cartilage cells were obviously in a cluster form, the layer structure was disordered, most tidal lines were not complete and distorted, and multiple tidal lines appeared in some regions; for the 1 Hz treatment group, the surface of the cartilage was rough, the cartilage cells were partially in a cluster form, the layer structure was disordered, and most tidal lines were not complete; for the 20 Hz treatment group, the surface of the cartilage was slightly rough, the cartilage cells tended to be in a dispersed distribution, and the tidal lines tended to be complete; for the 40 Hz treatment group, the surface of the cartilage tended to be smooth, the cartilage cells were distributed uniformly, and the tidal lines were complete; and for the sodium hyaluronate control group, the surface of the cartilage was slightly rough, the cartilage cells were distributed uniformly, and the tidal lines tended to be complete (FIG. 9). In the Mankin's rating, the score was the highest in the OA model group, and tended to decrease after the magnetic stimulation and sodium hyaluronate treatments. Here, the scores decreased the most significantly in the 40 Hz treatment group and the sodium hyaluronate control group, and both the differences were statistically significant (P<0.01) (Table 3).

The experimental results shown in FIG. 6 to FIG. 10 are described in detail below.

Figure 6:
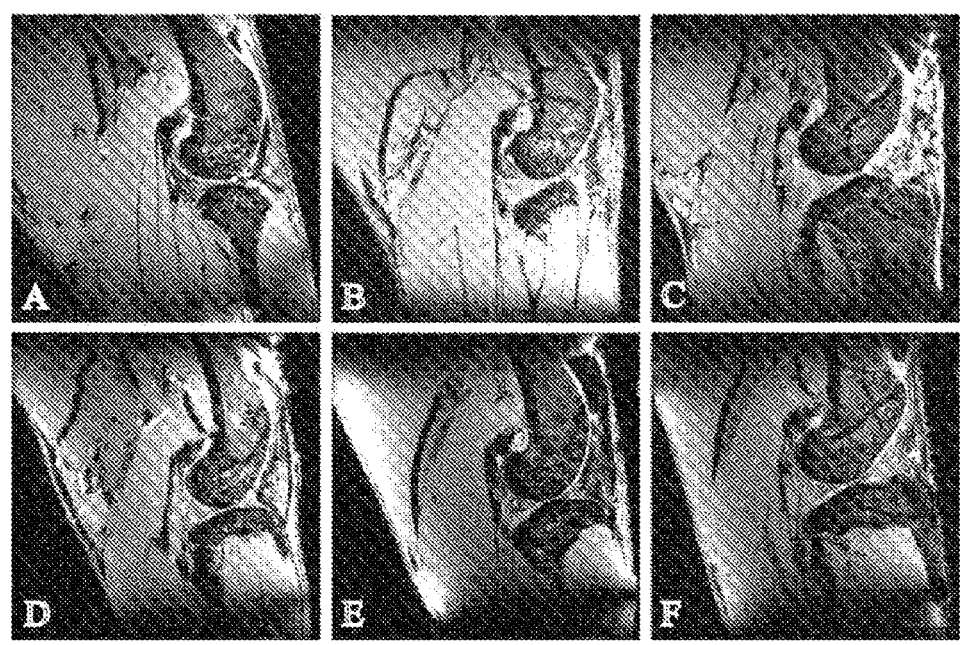
FIG. 6 shows a 3D nuclear magnetic resonance gradient recalled echo image of a rabbit knee joint in Example 1, in which A represents a sham operation group, B represents an injured cartilage model group, C represents an 1 Hz magnetic pulse treatment group, D represents a 20 Hz magnetic pulse treatment group, E represents a 40 Hz magnetic pulse treatment group, and F represents a sodium hyaluronate control group.

MRI analysis results were shown in FIG. 6. For the sham operation group, the surface profile of the articular cartilage of the knee joint was complete, and the thickness was normal (Fig. A); for the OA model group, the cartilage of the knee joint was lost in the whole layer and detached, and the subchondral bone was exposed (Fig. B); the injury of the articular cartilage in the 1 Hz treatment group was similar to that in the OA model group (Fig. C); for the 20 Hz treatment group, the surface profile of the articular cartilage was irregular, the thickness was not uniform, and the cartilage had defects with a shallow depth (Fig. D); for the 40 Hz treatment group, the surface profile of the cartilage was mildly irregular, and the thickness was slightly large (Fig. E); and for the sodium hyaluronate control group, the surface profile of the cartilage was mildly irregular, and some parts had defects (Fig. F).

The inflammatory factor indexes were shown in FIG. 7. The expression levels of IL-1β and NO in serum were determined by an ELISA method. As compared to the sham operation group, the IL-1β and NO levels in the OA model group increased significantly (P<0.05, P<0.01). As compared to the OA model group, the IL-1β and NO levels in the 40 Hz treatment group and the sodium hyaluronate control group dropped significantly, and the differences were statistically significant (P<0.05, P<0.01).

The comparison of removed rabbit knee joints was shown in FIG. 8. For the sham operation group, the surface of the articular cartilage of the knee joint was smooth and had a bright color (Fig. A); for the OA model group, defects and erosions were formed on the surface of the cartilage, deeply reaching the bone, and the subchondral bone was exposed (Fig. B); the 1 Hz treatment group had similar behaviors to those of the OA model group, having relatively severe injury (Fig. C); for the 20 Hz treatment group, the swelling of the right knee joint was significantly mitigated, there were defect and erosion on the surface of the articular cartilage, but the injury was relatively mild and had a limited range (Fig. D); for the 40 Hz treatment group, the gloss of the articular cartilage was slightly darker, and no obvious crack, erosion or ulcer was formed on the surface (Fig. E); and for the sodium hyaluronate control group, it could be seen that there was erosions and defects in some parts of the cartilage (Fig. F).

The comparison of the histological staining of the rabbit knee joints was shown in FIG. 9. For the sham operation group, the surface of the cartilage was smooth and flat, the cells were arranged orderly, the four-layered structure was clear, and the tidal lines were complete (A); for the OA model group, the surface of the cartilage was rough, the integrity was destroyed, the cartilage had defects, even the subchondral bone was exposed, the cartilage cells were aggregated, the cells were arranged disorderly, the four-layered structure was not clear, and the tidal lines were broken (B); for the 1 Hz treatment group, the surface of the cartilage was rough, the cartilage cells were partially in a cluster form, the layer structure was disordered, and most tidal lines were not complete (C); for the 20 Hz treatment group, the surface of the cartilage was slightly rough, the cartilage cells tended to be dispersedly distributed, and the tidal lines tended to be complete (D); for the 40 Hz treatment group, the surface of the articular cartilage was relatively flat, and the cartilage cells had an increased number, were distributed uniformly, and were normally colored (E); and for the sodium hyaluronate control group, the surface of the cartilage was coarse and not flat, the cartilage cells were dispersedly distributed, and the number of the cartilage cells decreased (F).

The electron microscope results of the cartilage cells (A: the sham operation group; B: the model group; C: the 40 Hz magnetic stimulation treatment group; and D: the sodium hyaluronate control group) were shown in FIG. 10 (A1-D1: ×8000; and A2-D2: ×20000). As seen from the electron microscope, for the sham operation group, the cartilage cell had a spindle shape or an oval shape, the nuclei was complete, the nuclear membrane was clear, there were irregular cytoplasmic processes on the surface of the cell, the density of the cytoplasm was uniform, a plenty of organelles were observed, the chromatins were distributed uniformly, and the texture of the collagen fiber was clear (A1, A2). For the model group, the matrix collagens were arranged disorderly, the profile of the cartilage cell was blurred, a large number of lipid droplets or vesicles appeared in the cytoplasm, the organelles in the cytosol decreased, the rough endoplasmic reticulum expanded or broke, vacuolar degradation of the mitochondria occurred, and the nuclear chromatin margination appeared (B1, B2). For the magnetic stimulation treatment groups, the cell morphology was substantially normal, the profile was clear, the cell and cell membrane were substantially complete, the collagen fibers were still clear, the shape of the nuclei was complete, the nuclear membrane was clear, the density of the cytoplasm slightly increased, and the organelles such as Golgi bodies increased (C1, C2). For the sodium hyaluronate control group, the morphology of the cartilage cell was substantially normal, the profile was clear, the collagen fibers were still clear, the rough endoplasmic reticulum expanded mildly, and the organelles increased (D1, D2).

Conclusion: the magneto-electric therapy of the present disclosure can mitigate the pathological progress of osteoarthritis and facilitate articular cartilage regeneration. The action mechanism may be directly related to the magnetically induced current in the tissue. The induced current in the tissue can not only act on individual cells, but also act on the whole macroscopic tissue, changing the medium between tissues and improving signal transmission, for example, down-regulating the expression levels of IL-1β and NO, thereby influencing and facilitating the recovery of cartilage tissue on multiple levels. Meanwhile, the magneto-electric therapy is a non-invasive therapy and is convenient to operate, having a broad prospect in clinical applications.

The foregoing descriptions are only preferred embodiments of the present disclosure, and are not intended to limit the protection scope of the present disclosure. Any variation, substitution or modification within the spirit and principle of the present disclosure is encompassed in the protection scope of the present disclosure.

The invention claimed is:

1. A magnetic pulse device, consisting of a magnetic pulse generator and one coil, wherein the coil has a shape, said shape creating an interior space to accommodate an entire entity of an animal's joint, and wherein the coil is made by winding one wire in a pattern which is formed from an axial projection of uniformly distributed concentric structures onto a surface of a model adapted to the animal's joint, such that when a magnetic pulse is applied to the coil, a uniform magnetic field distribution is produced in the interior space thereby inducing a uniform electrical excitation;
   wherein said magnetic pulse generator generates said magnetic pulse,
   wherein the uniformly distributed concentric structures comprise concentric circles and concentric squares, and
   wherein the shape of the coil comprises a parabola type, a hemi-ellipsoid type, a semi-cylinder type, and a half-spiral type structures.

2. The magnetic pulse device according to claim 1, wherein the magnetic field distribution produced by the coil is controlled depending on the number and density of the wires on the topological curved surface.

3. The magnetic pulse device according to claim 1, wherein the magnetic pulse device further comprises a magnetic pulse controller which controls a frequency, a duration and an intensity of the magnetic pulse produced by the magnetic pulse generator.

4. The magnetic pulse device according to claim 3, wherein the magnetic pulse controller controls the frequency of the magnetic pulse in a range from 10 Hz to 200 Hz.

5. The magnetic pulse device according to claim 1 for use in cartilage regeneration.

6. The magnetic pulse device according to claim 5, wherein the magnetic pulse device is used for applying a magnetic field to a body part of a mammal in which an injured cartilage tissue is located, wherein by applying the magnetic pulse with a frequency of from 10 Hz to 200 Hz to the coil, the uniform magnetic field distribution is produced in a region of the body part covered by the coil, thereby achieving the uniform electrical excitation magnetically induced.

7. A method for cartilage regeneration by using a magnetic pulse device according to claim 1, comprising: applying a pulse magnetic field with a magnetic pulse device to a body part of a mammal in which an injured cartilage tissue is located, wherein the magnetic pulse device comprises a magnetic pulse generator and a coil, and by applying a magnetic pulse with a frequency of from 40 Hz to 80 Hz and an intensity of from 1000 Gauss to 30,000 Gauss to the coil, a uniform magnetic field distribution is produced in a region of the body part covered by the coil, thereby achieving a uniform magnetically induced electrical excitation.

8. The method according to claim 1, wherein a duration of the magnetic pulse is from 10 μsec to 1000 μsec.

9. The method according to claim 1, wherein a total duration for each treatment is from 1 minute to 30 minutes, and a total treatment numbers is from 10 to 500.

10. The method according to claim 1, wherein the cartilage tissue comprises an articular cartilage tissue.

11. The method according to claim 1, wherein the mammal comprises human, horse, dog, cat, rabbit, cattle, sheep, and pig.

12. A coil for a magnetic pulse device, wherein the coil has a shape, said shape creating an interior space to accommodate an entire entity of an animal's joint, and the coil is made by winding one wire in a pattern formed from a projection of uniformly distributed concentric structures, said projection being an axial projection of the uniformly distributed concentric structures onto a surface of a model adapted to the animal's joint, such that when a magnetic pulse is applied to the coil, a uniform magnetic field distribution is produced in the interior space, thereby inducing a uniform electrical excitation, wherein the uniformly distributed concentric structures comprise concentric circles and concentric square, and wherein the shape of the coil comprises a parabola type, a hemi-ellipsoid type, a semi-cylinder type, and a half-spiral type structures.

* * * * *